United States Patent

Tersteegen et al.

[11] 4,429,852
[45] Feb. 7, 1984

[54] ADAPTER

[76] Inventors: Bernd Tersteegen; Gunter Van Endert, both of Karlstrasse 17-19, 4000 Dusseldorf, Fed. Rep. of Germany

[21] Appl. No.: 482,017

[22] Filed: Apr. 11, 1983

Related U.S. Application Data

[63] Continuation of Ser. No. 313,157, Oct. 20, 1981.

[30] Foreign Application Priority Data

Oct. 21, 1980 [DE] Fed. Rep. of Germany ....... 3039591

[51] Int. Cl.³ ...................... F16L 55/14; A61B 17/00
[52] U.S. Cl. ...................................... 251/9; 128/346; 604/250; 24/543
[58] Field of Search .................. 251/4, 6, 9, 10, 342; 604/246, 250, 34; 128/346, 325, 214.2, 247, 214 R, 214 G; 24/255 R, 259; D24/27; 81/9.3

[56] References Cited

U.S. PATENT DOCUMENTS

| | | | |
|---|---|---|---|
| 350,850 | 10/1886 | Tatum | 251/10 |
| 1,361,770 | 12/1920 | O'Connor | 251/10 |
| 1,959,074 | 5/1934 | Bloxsom | 251/6 |
| 2,682,874 | 7/1954 | Hickey | 251/10 X |
| 2,722,932 | 11/1955 | Hickey | 604/34 X |
| 3,135,259 | 6/1964 | Evans | 604/34 X |
| 3,329,391 | 7/1967 | Deane | 128/346 |
| 4,106,508 | 8/1978 | Berlin | 128/325 X |
| 4,136,694 | 1/1979 | Kuehn | 128/214.2 X |
| 4,235,412 | 11/1980 | Rath et al. | 251/10 |
| 4,326,518 | 4/1982 | Williams | 128/214.2 |

FOREIGN PATENT DOCUMENTS

| | | | |
|---|---|---|---|
| 2331297 | 3/1975 | Fed. Rep. of Germany | 251/4 |
| 745844 | 3/1956 | United Kingdom | 251/6 |

OTHER PUBLICATIONS

*Dura–Clamp Flow Valves for Flexible Tubing,* Thermoplastic Scientifics, Inc., ©1979.

*Primary Examiner*—C. Fred Rosenbaum
*Assistant Examiner*—Michelle N. Lester
*Attorney, Agent, or Firm*—Dressler, Goldsmith, Shore, Sutker & Milnamow, Ltd.

[57] ABSTRACT

An adapter for connecting tubes is provided with an integrally formed clamp which may be manually manipulated from an open to a closed position to at least constrict a tube. The adapter further includes integral latch means, which is manually movable to a closed position by cam action, and which is releasably held in the closed position by the inherent elastic nature of the adapter body.

2 Claims, 4 Drawing Figures

ADAPTER

This application is a continuation of application Ser. No. 313,157, filed Oct. 20, 1981.

The invention relates to an adapter for the establishment of connections in medically used tube systems.

Such adapters are constructed, for example, in the form of so-called Luer adapters and present ordinarily a self-locking conical connection. They serve to establish the connection of a tube with another tube, or with a further tube system. Adapters are used, for example, to establish a connection between the connecting tube of a cannula provided for hemodialysis with an extra-corporal system, in urological cathers, in a taking of blood, or the like.

It is further known and usual to place on the connecting tube connected or connectable with the adapter a clamp, by which the opening cross-section of the connecting tube can be reduced to zero. Thereby fluid or air is prevented from escaping from the system or entering it in the removal of the adapters or of the tubes. For this there are frequently used so-called Pean clamps, which are formed in the manner of a blunt scissors. Such clamps are voluminuos, heavy and expensive. In various areas of medicine, thus, for example, for use in hemodialysis, disposable cannulas and disposable tube systems have become usual, which for hygienic reasons are thrown away after use (so-called "disposables"). Especially in the case of a single use, the use of such Pean clamps is economically insupportable. The proposal has already been made to slip onto the tubes a clamp surrounding the tube on the outside. The clamp presents a spring tongue which is snappable in place with an arresting device in the oppositely situate clamp part in such a way that the tube in the clamping position is clamped between two camtype parts. It is disadvantageous here that the clamp, in the setting up of the tube system which in the case of cannulas, for example, consists of cannula tube, cannula holder, under some circumstances cannula hand grip, connecting tube and adapter, must be manufactured separately and slipped onto the connecting tube for the assembly. Furthermore, the clamp is freedly slidable over the entire length of the connecting tube, so that especially in the case of complicated tube systems it is often necessary to look for and find the clamp before operating it.

Underlying the invention is the problem of improving the adapters used for the establishment of connections in medically used tube systems in such a way that these are more favorable than hitherto in respect to the manufacture and in respect to the handling.

This problem is solved according to the invention by the means that the adapter presents means for cross-section reduction of the tube, which is provided for action from outside the tube. It is especially to the point if the means for cross-section reduction is made in one piece with the adapter or adapter body.

Here it is advantageous that now the means for the cross-section reduction can be produced in common and preferably in one piece with the adapter, so that not only the manufacture, but also the assembling becomes substantially cheaper and simpler.

In accordance with a further advantageous aspect of the invention the means for cross-section reduction presents an arresting device. This can be adjustable stepwise or stagelessly to different opening widths of the tube down to the opening cross-section zero.

According to a further feature of the invention it can be provided that the device for cross-section reduction presents a support and a clamping member arranged opposite the support and formed in correspondence to this. The clamping member can be arranged on a tongue movable toward and away from the support. The support can present at least one support clamping member. Further, it can be provided that the clamping member is arranged offset with respect to the supporting clamping member or support clamping members in the longitudinal direction of the tube. This has the advantage that this clamping arrangement is suited for connecting tubes of different wall thicknesses.

According to another feature of the invention it can be provided that the support presents a lead-through opening embracing the tube on all sides. This offers the advantage that the tube cannot slip out. Further, the part presenting the lead-through opening can simultaneously be used as arresting device.

According to a further feature of the invention it can be provided that the support or the wall surrounding the lead-through opening and a catch on the tongue or the clamping member cooperate to form an arresting device for holding the clamping device in a closed position.

In accordance with another aspect of the invention the support is arcuately shaped in correspondence to the outside contour of the tube and the clamping member —with account taken of the thickness of the tube wall thickness—is correspondingly arcuately shaped. This requires less width for the arrangement than if the tube were pressed flat on both sides in such a way that the oppositely situated tube walls lie against one another on opposite sides of the longitudinal axis of the tube.

The clamping member is preferably pivotable about an axis lying transversely to the longitudinal direction of the tube, so that a one-handed operation is possible both for right-handed people and also for left-handed people.

By the term "adapter" in the sense of the present invention it is not meant to limit the invention to the uses specifically mentioned and represented in the examples of execution, but instead in the broadest sense, the invention is applicable to all components connected to or connectable with tubes in medically used tube systems, for examples distributor pieces, injection places, drip chambers or the like.

The invention is explained in detail in the following with the aid of the examples of execution represented in the drawings.

Figure 1:
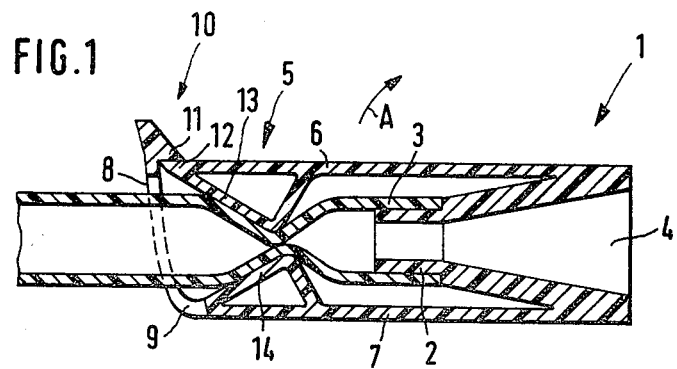
FIG. 1 is a schematic longitudinal section through a first embodiment of the adapter, with a tube connected to it, and with the tube comprising means of the adapter being shown in closed position.

An adapter 1 defines an internal hollow sleeve 2 for the slipping on of a tube 3. Further, there is provided a conically widening opening 4, which serves for the inserting of a correspondingly conically formed connecting piece (not shown), with which there can be established a connection with another tube or another tube system. It would, of course, obviously also be possible to form the connection of the tube 3 with the adapter as a plug-in connection rather than a slip-on connection, as shown. The adapter presents a tube compressing means formed integrally with it, designated as a whole by reference numeral 5 for the cross-section reduction of the tube 3. The tube compressing means has, opposite the tube 3, a tongue 6 extending substantially in the longitudinal direction of the tube 3 and a support 7 is provided on the opposite side of the tube. The support 7 is constructed relatively rigid and provided with an end piece 8 extending upwardly and forwardly of the tongue 6, in which end piece there is provided a lead-through opening 9 for the tube. At the left end of the adapter, as viewed in FIG, 1, there is provided an arresting device 10 with a snap-in rest 11, into which the snap-in end 12 of the elastically formed tongue 6 can snap in place. Lying opposite, but somewhat offset against one another in longitudinal direction of the tube there are provided clamping members constructed as cams 13 and 14, by means of which the opening cross-section of the tube 3 can be reduced. FIG. 1 shows the position in which the opening cross-section of the tube is reduced to zero. The arresting device is represented in simplified form and can present several snap-in places for several opening widths or also be formed stagelessly adjustable to different opening widths. When the end of the elastic tongue is not arrested in the arresting device 10, the tongue 6 is swung up in swinging direction A.

The adapter of the present invention is preferably molded from a suitable plastic material, such as acrylonitrite-butadiene-styrene, polycarbonate, polyethylene or polypropylene, as will be apparent to those skilled in the art. The selected material should have enough resiliency to bias the tongue to an open position, and enough flexibility as to be readily moved to a closed position by finger pressure. The tongue may be released for movement to the open position by flexing end piece 8 outwardly.

Figure 2:
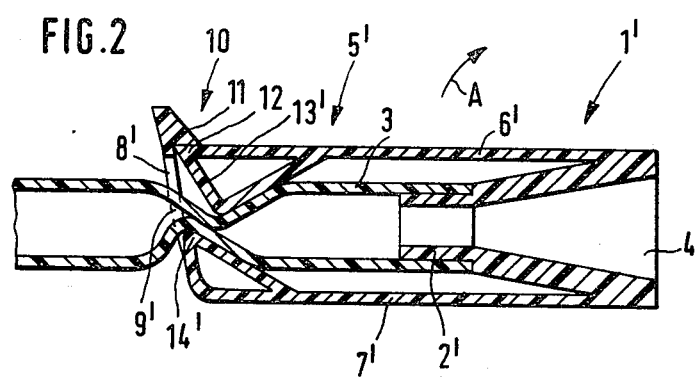
FIG. 2 is a view corresponding to FIG. 1 for another embodiment of the invention.

The adapter designated in its entirety by reference number 1' in FIG. 2 differs from the adapter shown in FIG. 1 merely in the arrangement of the clamping members. Parts corresponding to one another bear the same reference numbers and are not again explained. The upwardly extending end piece 8' presents a lead-through opening 9' for the tube 3, the other end of which is simultaneously formed as clamping member 14'. Correspondingly, the clamping member 13' is formed on the lower surface of the elastic tongue 6' so that the tube 3 is clamped at the left end of the adapter 1; rather than inwardly of the adapter 1, as shown in FIG. 1.

Figure 3:
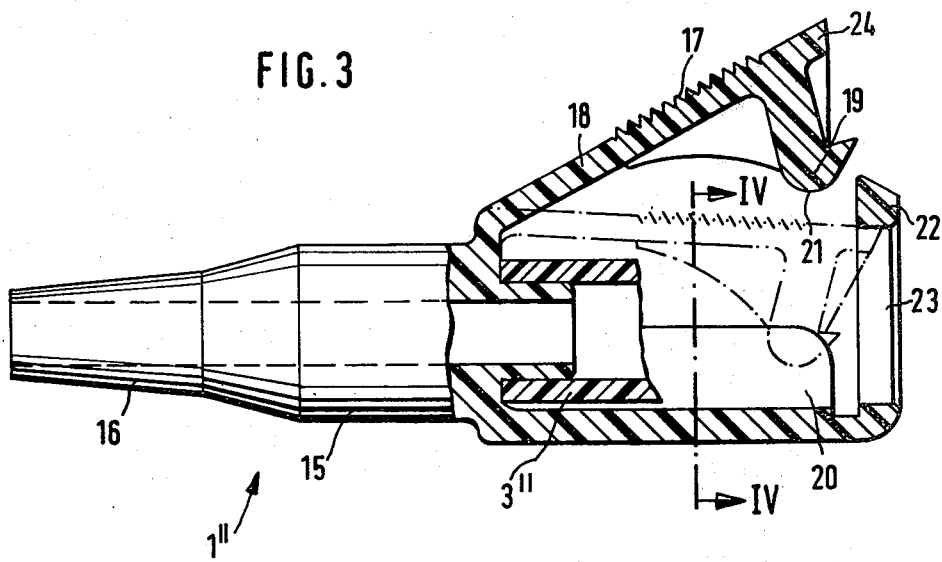
FIG. 3 is a side view, partly in cross-section, of another embodiment of the invention.
Figure 4:
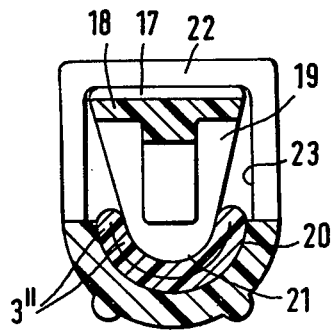
FIG. 4 is a section along line IV—IV in FIG. 3.

The adapter illustrated in FIGS. 3 and 4 and designated with 1" presents on its adapter casing 15 a conically converging plug-in part 16. The main difference from the adapter embodiments illustrated in FIGS. 1 and 2 lies in that the support 20 lying opposite a tongue 18 and a clamping member 19 is formed in correspondence of the outer contour of the tube, respectively to the outer radius of the tube 3". The face end 21 of the clamping member 19 is correspondingly arcuately shaped, and in the dimensioning of the radius the doubled tube wall thickness to be clamped in is taken into consideration. As is evident from FIG. 4, the maximum outside diameter of the tube 3" in the clamped position is not greater than the outside diameter of the tube in the open position. The adapter presents on its right-hand end as viewed in FIG. 3, an end piece 22 formed in the manner of a frame with a tube lead-through opening 23. The tongue 18 can snap in place with a snap-in element 24 into the part 22. For this purpose the parts are constructed correspondingly elastic. The snapped-in position in which the opening cross-section of the tube is reduced to zero is shown in FIG. 3 in broken lines (without representation of the tube). The section representation according to FIG. 4 corresponds to a section through FIG. 3 in the snapped-in position, the tube being represented here.

What is claimed is:

1. An adapter for connecting first and second tubes comprising: an adapter body; first connecting means on said body for attachment to said first tube; second attachment means on said body for attachment to said second tube; manually movable compression means formed integrally with said body comprising a clamping member movable with respect to said body and having an arcuately shaped tube engaging portion, said compression means being movable under manual pressure from an open position to a closed position wherein one of said tubes is at least partially constricted; said body including an integrally formed support having an arcuately shaped tube engaging surface, said support being positioned opposite of said clamping member with respect to said one tube for cooperation with said clamping member when said compression means is positioned in said closed position to compress said one tube between said clamping member and said support, said arcuately shaped tube engaging surface being generally defined by a radius greater than a further radius generally defining said arcuately shaped tube engaging portion; said adapter further including latching means formed integrally with said body and formed by a portion of a wall defined by an opening through which said one tube extends, said wall being integrally formed with said support; said latching means being adapted to engage and coact with catch means formed integrally with said compression means to releasably retain said compression means in said closed position.

2. An adapter as set forth in claim 1, wherein said radius which generally defines said arcuately shaped tube engaging surface corresponds to the outer radial dimension of said one tube, and said further radius generally defining said arcuately shaped tube engaging portion corresponds to the outer radial dimension of said one tube less twice the wall thickness of said one tube.

* * * * *